US006782292B2

(12) United States Patent
Whitehurst

(10) Patent No.: US 6,782,292 B2
(45) Date of Patent: Aug. 24, 2004

(54) SYSTEM AND METHOD FOR TREATMENT OF MOOD AND/OR ANXIETY DISORDERS BY ELECTRICAL BRAIN STIMULATION AND/OR DRUG INFUSION

(75) Inventor: Todd K. Whitehurst, Sherman Oaks, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 362 days.

(21) Appl. No.: 09/882,560

(22) Filed: Jun. 15, 2001

(65) Prior Publication Data

US 2002/0013612 A1 Jan. 31, 2002

Related U.S. Application Data

(60) Provisional application No. 60/212,871, filed on Jun. 20, 2000.

(51) Int. Cl.[7] .............................................. A61N 1/18
(52) U.S. Cl. ................................................... 607/45
(58) Field of Search ........................ 607/3, 45, 72, 607/115–117, 120, 153; 128/898; 604/20, 21, 53, 890.1, 891.1, 892.11, 65–67, 93

(56) References Cited

U.S. PATENT DOCUMENTS

| | | | |
|---|---|---|---|
| 5,092,835 A | 3/1992 | Schurig et al. | 600/9 |
| 5,094,242 A | 3/1992 | Gleason et al. | 128/642 |
| 5,193,539 A | 3/1993 | Schulman et al. | 128/419 |
| 5,193,540 A | 3/1993 | Schulman et al. | 128/419 |
| 5,299,569 A | 4/1994 | Wernicke et al. | 607/45 |
| 5,312,439 A | 5/1994 | Loeb | 607/2 |
| 5,324,316 A | 6/1994 | Schulman et al. | 607/61 |
| 5,405,367 A | 4/1995 | Schulman et al. | 607/61 |
| 5,540,734 A | 7/1996 | Zabara | 607/46 |
| 5,975,085 A | 11/1999 | Rise | 128/898 |
| 6,016,449 A | 1/2000 | Fischell et al. | 607/45 |

(List continued on next page.)

FOREIGN PATENT DOCUMENTS

| | | |
|---|---|---|
| WO | 8707511 | 12/1987 |
| WO | 9400188 | 1/1994 |
| WO | 9521591 | 8/1995 |
| WO | 9837926 | 9/1998 |
| WO | 9843700 | 10/1998 |
| WO | 9843701 | 10/1998 |
| WO | 0160450 | 8/2001 |

OTHER PUBLICATIONS

Baxter, et al., "Cerebral Metabolic Rates for Glucose in Mood Disorders. Studies with Positron Emission Tomography and Fluorodeoxyglucose F 18", Arch Gen Psychiatry, 42:5 441–7 (May 1985).
Baxter, et al., "Trazodone Treatment Response in Obsessive–Compulsive Disorder—Correlated with Shifts in Glucose Metabolism in the Caudate Nuclei", Psychopathology, 20 Suppl 1 114–22 (1987).
Baxter, et al., "Cerebral Glucose Metabolic Rates in Nondepressed Patients with Obsessive–Compulsive Disorder", Am J Psychiatry, 145:12 1560–3 (Dec. 1988).

(List continued on next page.)

Primary Examiner—Jeffrey R. Jastrzab
(74) Attorney, Agent, or Firm—Laura Haburay Bishop; Bryant R. Gold

(57) ABSTRACT

A system and method for introducing one or more stimulating drugs and/or applying electrical stimulation to the brain to treat mood and/or anxiety disorders uses an implantable system control unit (SCU), specifically an implantable signal/pulse generator (IPG) or microstimulator with two or more electrodes in the case of electrical stimulation, and an implantable pump with one or more catheters in the case of drug infusion. In cases requiring both electrical and drug stimulation, one or more SCUs are used. Alternatively and preferably, when needed, an SCU provides both electrical stimulation and one or more stimulating drugs. In a preferred embodiment, the system is capable of open- and closed-loop operation. In closed-loop operation, at least one SCU includes a sensor, and the sensed condition is used to adjust stimulation parameters.

18 Claims, 11 Drawing Sheets

U.S. PATENT DOCUMENTS

| | | | | |
|---|---|---|---|---|
| 6,051,017 | A | 4/2000 | Loeb et al. | 607/1 |
| 6,061,593 | A | 5/2000 | Fischell et al. | 600/544 |
| 6,128,537 | A | 10/2000 | Rise | 607/45 |
| 6,167,311 | A | 12/2000 | Rezai | 607/45 |
| 6,263,237 | B1 | 7/2001 | Rise | 607/3 |
| 6,415,184 | B1 | 7/2002 | Ishikawa et al. | |
| 6,418,344 | B1 | 7/2002 | Rezai et al. | 607/45 |
| 6,427,086 | B1 * | 7/2002 | Fischell et al. | 607/45 |
| 6,463,328 | B1 * | 10/2002 | John | 607/45 |
| 6,464,687 | B1 | 10/2002 | Ishikawa et al. | |
| 6,597,954 | B1 * | 7/2003 | Pless et al. | 607/62 |
| 2002/0161403 | A1 * | 10/2002 | Meadows et al. | 607/1 |

OTHER PUBLICATIONS

Baxter, et al., "Reduction of Prefrontal Cortex Glucose Metabolism Common to Three Types of Depression", Arch Gen Psychiatry, 46:3 243–50 (Mar. 1989).
Baxter, L.R., "Brain Imaging as a Tool in Establishing a Theory of Brain Pathology in Obsessive Compulsive Disorder", J Clin Psychiatry, 51 Suppl 22–5 (Feb. 1990).
Baxter, et al., "Caudate Glucose Metabolic Rate Changes with Both Drug and Behavior Therapy for Obsessive–compulsive Disorder", Arch Gen Psychiatry, 49:9 681–9 (Sep. 1992).
Bench, et al., "The Anatomy of Melancholia–Focal Abnormalities of Cerebral Blood Flow in Major Depression", Psychol Med, 22(3):607–15 (Aug. 1992).
Yavari, et al., "Decreased Raphe Unit Activity in a Rat Model of Endogenous Depression", Brain Res., 611(1):31–6, (May 14, 1993).
Joffe, et al., "Augmentation Strategies", J Clin Psychiatry, 57 (Suppl 7): 25–31 (1996).
Ebmeier, et al., "Cerebral Perfusion Correlates of Depressed Mood", Br J Psychiatry, 170:77–81 (Jan. 1997).
Stockmeier, et al., "Serotonin Receptors in Suicide Victims with Major Depression", Neuropsychopharmacology, 16(2): 162–73 (Feb. 1997).
Drevets, et al., "Subgenual Prefrontal Cortex Abnormalities in Mood Disorders", Nature, 386(6627): 824–7 (Apr. 24, 1997).
Kirkcaldie, et al., "Transcranial Magnetic Stimulation as Therapy for Depression and Other Disorders", Aust N Z J Psychiatry, 31(2): 264–72 (Apr. 1997).
Klimek, et al., "Reduced Levels of Norepinephrine Transporters in the Locus Coeruleus in Major Depression", J Neurosci, 17(21): 8451–8 (Nov. 1, 1997).
Drevets, W.C., "Functional Neuroimaging Studes of Depression: The Anatomy of Melancholia", Annu Rev Med, 49:341–61 (1998).
Saxna, et al., "Neuroimaging and Frontal–Subcortical Circuitry in Obsessive–Compulsive Disorder", BR J Psychiatry Suppl, 35 26–37 (1998).
Galynker, et al., "Hypofrontality and Negative Symptoms in Major Depressive Disorder", J Nucl Med 39(4):608–12 (Apr. 1998).
Abercrombie, et al., "Metabolic Rate in the Right Amygdala Predicts Negative Affect in Depressed Patients", Neuroreport, 9(14): 3301–7 (Oct. 5, 1998).
Brody, et al., "FDG–PET Predictors of Response to Behavioral Therapy and Pharmacotherapy in Obsessive Compulsive Disorder", Psychiatry Res, 84:1 1–6 (Nov. 9, 1998).
Davidson, et al., "Regional Brain Function, Emotion and Disorders of Emotion", Curr Opin Neurobiol, 9(2): 228–34 (Apr. 1999).
Bejjani, et al., "Transient Acute Depression Induced by High–Frequency Deep Brain Stimulation", New England Journal of Medicine, 340(19): 1476–80 (May 13, 1999).
Pridmore, et al., "Transcranial Magnetic Stimulation in the Treatment of Psychiatric Disorders", Psychiatry Clin Neurosci, 53(5): 541–8 (Oct. 1999).
Rush, et al., "Vagus Nerve Stimulation (VNS) for Treatment–Resistant Depressions: A Multicenter Study", Biological Psychiatry, 47:276–286, (2000).
Sackheim, et al., "The Effects of Vagus Nerve Stimulation on cognitive Performance in Patients with Treatment–Resistant Depression", Neuropsychiatry, Neuropsychology, and Behavioral Neurology, vol. 14, No. 1, 53–62 (2001).
Davis, et al., "The Amygdala: Vigilance and Emotion", Mol Psychiatry, 13–34 (Jan. 2001).

* cited by examiner

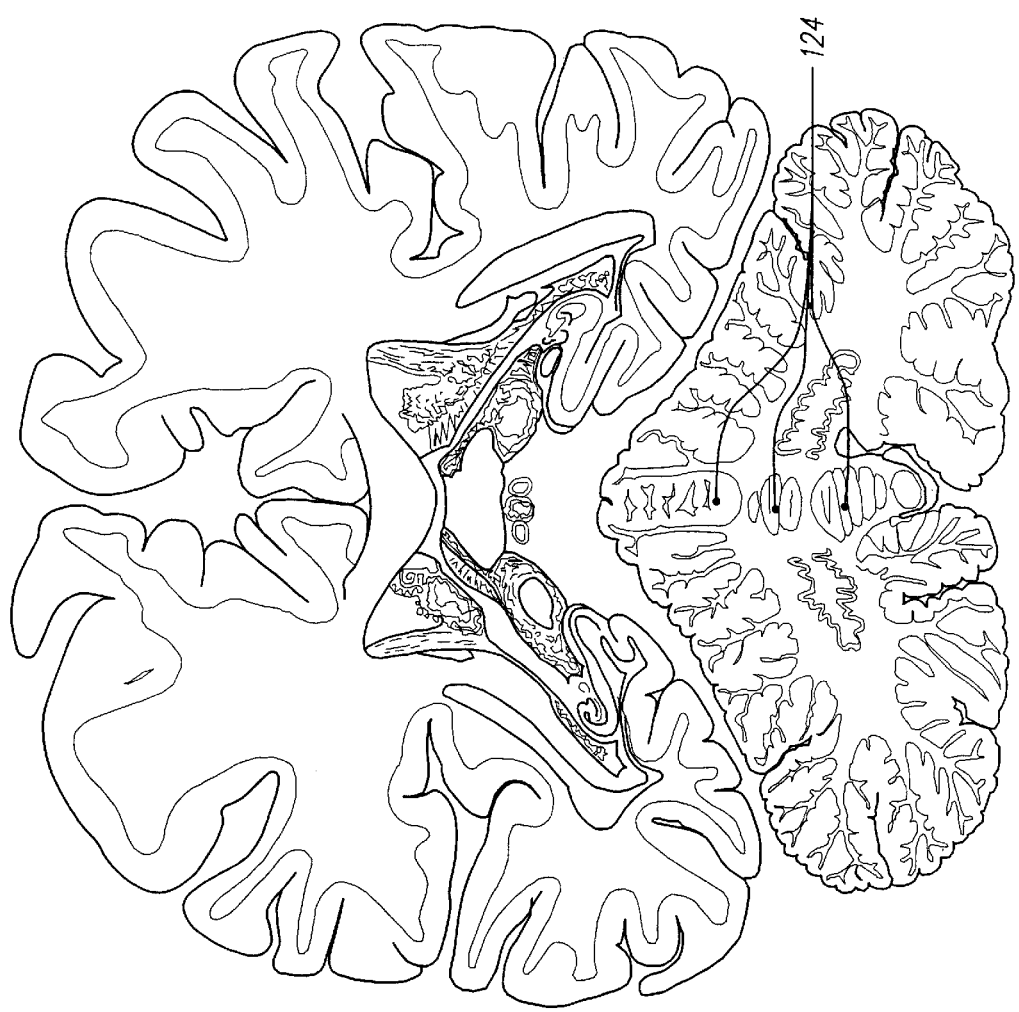

SYSTEM AND METHOD FOR TREATMENT OF MOOD AND/OR ANXIETY DISORDERS BY ELECTRICAL BRAIN STIMULATION AND/OR DRUG INFUSION

The present application claims the benefit of U.S. Provisional Application Serial No. 60/212,871, filed Jun. 20, 2000, which application is incorporated herein by reference in its entirety.

FIELD OF THE INVENTION

The present invention generally relates to implantable drug delivery and electrical stimulation systems and methods, and more particularly relates to utilizing one or more implantable devices to deliver electrical stimulation and/or one or more stimulating drugs as a treatment for mood and/or anxiety disorders.

BACKGROUND OF THE INVENTION

Recent estimates indicate that more than 19 million Americans over the age of 18 years experience a depressive illness each year. The American Psychiatric Association recognizes several types of clinical depression, including Mild Depression (Dysthymia), Major Depression, and Bipolar Disorder (Manic-Depression). Major Depression is defined by a constellation of chronic symptoms that include sleep problems, appetite problems, anhedonia or lack of energy, feelings of worthlessness or hopelessness, difficulty concentrating, and suicidal thoughts. Approximately 9.2 million Americans suffer from Major Depression, and approximately 15 percent of all people who suffer from Major Depression take their own lives. Bipolar Disorder involves major depressive episodes alternating with high-energy periods of rash behavior, poor judgment, and grand delusions. An estimated one percent of the American population experiences Bipolar Disorder annually.

Significant advances in the treatment of depression have been made in the past decade. Since the introduction of Selective Serotonin Reuptake Inhibitors (SSRIs), e.g., Prozac® antidepressant, many patients have been effectively treated with anti-depressant medication. New medications to treat depression are introduced almost every year, and research in this area is ongoing. However, an estimated 10 to 30 percent of depressed patients taking an antidepressant are partially or totally resistant to the treatment. Those who suffer from treatment-resistant depression have almost no alternatives.

Electroconvulsive Therapy (ECT) is an extreme measure that is used today to treat such patients. In ECT, a low-frequency electrical signal is sent through the brain to induce a 30- to 60-second general seizure. The side effects include memory loss and other types of cognitive dysfunction.

Repetitive Transcranial Magnetic Stimulation (rTMS) is currently being explored as another therapy for depression. Kirkcaldie et al. (1997) reported a greater than 50 percent response rate when applying rTMS to the left dorsolateral prefrontal cortex of 17 depressed patients. In addition, a company headquartered in Houston, Tex. is currently exploring the application of vagus nerve stimulation to treatment-resistant depression; Rush, et al. (1999) report a success rate of 40–50 percent in a recent study of 30 patients.

Deep Brain Stimulation (DBS) has been applied to the treatment of central pain syndromes and movement disorders, and it is currently being explored as a therapy for epilepsy. For instance, U.S. Pat. No. 6,016,449 to Fischell, et al. discloses a system for the electrical stimulation of areas in the brain for the treatment of certain neurological diseases such as epilepsy, migraine headaches and Parkinson's disease. However, Fischell et al. do not teach or suggest the use of such a system for the treatment of mood disorders, such as depression.

As was recently reported by Bejjani, et al. (1999), a patient responded to DBS of an area near the thalamus during the therapeutic placement of a stimulator for tremor, by lapsing into a sudden and marked depressive episode. The depression ceased within a couple of minutes after stimulation was halted, and the patient demonstrated a rebound ebullience. This phenomenon was repeated in the same patient several weeks later for purposes of verification.

New functional imaging techniques have led to the identification of several sites in the brain that demonstrate abnormal characteristics (e.g., hypoperfusion) in depression. Several regions of the brain have been identified as having decreased blood flow or metabolism in depressed patients compared to controls. In an important 1997 study, Drevets et al. reported that the subgenual prefrontal cortex (i.e., the anterior cingulate gyrus ventral to the corpus callosum) demonstrated decreased blood flow or metabolism in patients with Major Depression and with Bipolar Disorder compared with psychiatrically normal controls.

Similarly, Ebmeier et al. (1997), in a review of several studies, reported that the anterior cingulate gyrus demonstrates decreased blood flow or metabolic activity in depressed patients. In a 1999 review, Davidson et al. cite several reports that indicate that the left anterior cingulate gyrus demonstrates decreased activity in depression and furthermore demonstrates increased activity in depressed patients who respond to antidepressant medication.

Galynker et al. (1998) reported that decreased blood flow in the left dorsolateral prefrontal cortex correlated with severity of negative symptoms in depressed patients. (The left dorsolateral prefrontal cortex is the primary target of rTMS in the treatment of depression.) Drevets, in an extensive 1998 review, generalizes these results to suggest that the dorsal prefrontal cortex demonstrates decreased activity in depression while the ventral prefrontal cortex demonstrates increased activity.

Bench et al. (1992) reported decreased blood flow in the left anterior cingulate gyrus and the left dorsolateral prefrontal cortex in depressed patients as compared with controls, and further reported increased blood flow in the cerebellar vermis in depressed patients with depression-related cognitive impairment.

As stated above, Drevets reported that the ventral prefrontal cortex demonstrates increased activity in depressed patients, and further reported evidence that blood flow and metabolism are abnormally increased in the medial thalamus in patients with Major Depression and Bipolar Disorder as compared with controls. As also stated above, Bench reported abnormally increased blood flow in the cerebellar vermis in depressed patients with depression-related cognitive impairment. Abercrombie et al. (1998) reported that the metabolic rate in the right amygdala predicts negative affect in depressed patients (although no absolute difference was found between depressed and control subjects).

Recent studies of neurotransmitter receptors in the brains of patients with depression also suggest possible sites of the brain that are abnormal in depression. Stockmeier et al. (1997) reported an increased number of serotonin receptors in the dorsal raphe nucleus of suicide victims with major depression as compared with psychiatrically normal controls. Similarly, Yavari et al. (1993) reported decreased activity in the dorsal raphe nucleus in a rat model of endogenous depression. Klimek et al. (1997) reported reduced levels of norepinephrine transporters in the locus coeruleus in major depression. These findings corroborate existing anatomical evidence regarding the functions of these areas.

In 1998, Saxena et al. performed a study of the pathophysiology of obsessive-compulsive disorder. They found that at least a subgroup of patients with obsessive-compulsive disorder may have abnormal basal ganglia development. They observed that obsessive-compulsive disorder symptoms are associated with increased activity in the orbitofrontal cortex, caudate nucleus, thalamus, and anterior cingulate gyrus.

The dorsal and median raphe nuclei, which course within the medial forebrain bundle, the dorsal longitudinal fasciculus, and the medial longitudinal fasciculus, have long been known to have major serotonergic projections to the limbic system. Medications that block serotonin reuptake (thus increasing its level) are effective therapy for depression, panic disorder, obsessive-compulsive disorder, and other mood and anxiety disorders.

The locus coeruleus, which lies near the floor of the fourth ventricle, has major noradrenergic projections to virtually the entire central nervous system, including the cerebral cortex, the limbic system, and the hypothalamus. Medications that dually block serotonin and norepinephrine reuptake (and thus increase their levels) are effective therapy for depression, panic disorder, obsessive-compulsive disorder, and other mood and anxiety disorders.

Low-frequency electrical stimulation (i.e., less than 50–100 Hz), has been demonstrated to excite neural tissue, leading to increased neural activity. Similarly, excitatory neurotransmitters, agonists thereof, and agents that act to increase levels of an excitatory neurotransmitter(s) have been demonstrated to excite neural tissue, leading to increased neural activity. Inhibitory neurotransmitters have been demonstrated to inhibit neural tissue, leading to decreased neural activity; however, antagonists of inhibitory neurotransmitters and agents that act to decrease levels of an inhibitory neurotransmitter(s) have been demonstrated to excite neural tissue, leading to increased neural activity.

High-frequency electrical stimulation (i.e., more than about 50–100 Hz) is believed to have an inhibitory effect on neural tissue, leading to decreased neural activity. Similarly, inhibitory neurotransmitters, agonists thereof, and agents that act to increase levels of an inhibitory neurotransmitter (s) have an inhibitory effect on neural tissue, leading to decreased neural activity. Excitatory neurotransmitters have been demonstrated to excite neural tissue, leading to increased neural activity; however, antagonists of excitatory neurotransmitters and agents that act to decrease levels of an excitatory neurotransmitter(s) inhibit neural tissue, leading to decreased neural activity.

Various electrical stimulation and/or drug infusion devices have been proposed for treating neurological disorders. Some devices stimulate through the skin, such as electrodes placed on the scalp. Other devices require significant surgical procedures for placement of electrodes, catheters, leads, and/or processing units. These devices may also require an external apparatus that needs to be strapped or otherwise affixed to the skin.

While some patents exist that teach drug infusion and/or electrical stimulation for treatment of neurological disorders (see, e.g., U.S. Pat. Nos. 5,092,835; 5,299,569; 5,540,734; 5,975,085; 6,128,537; and 6,167,311), the inventors know of no device that targets the areas of the brain previously discussed and provides chronic stimulation via a device that is implanted completely within the head of the patient. For instance, in U.S. Pat. No. 6,128,537 (the '537 patent), the infusion pump (reference number 10), the electrical signal generator (reference number 16), or both devices are implanted in the body of the patient, but not in the head of the patient. In the figures depicting the implanted devices (FIGS. 1, 4, 5, 6, and 7), it is readily seen that a catheter (number 22 in FIGS. 1, 4, 6, and 7) or a cable (numbered 42' in FIG. 5) is tunneled through, at the very least, the neck of the patient in order to allow a drug or electrical stimulation to reach a desired target in the brain. Further, note column 6, lines 8–10 of the '537 patent: "Signal generator 16 is implanted in a human body, preferably in a subcutaneous pocket located over the chest cavity or the abdomen." There is no recognition in the '537 patent that tunneling catheters and/or cables from the chest to the head, or from the abdomen to the head, is a problem to be overcome.

On the other hand, U.S. Pat. No. 6,167,311 (the '311 patent) seems to recognize this problem, but offers no solution. Additionally, the '311 patent acknowledges that there is no presently available solution, and that therefore, the signal generator "must be disposed at a remote site in the patient's body." Note column 7, lines 57–62 of the '311 patent: "As is readily obvious to anyone who has witnessed the unnecessary surgical procedure associated with the remote localization of the power source, it is desirable the burr cap structure itself comprise the signal source. However, as that option is not presently available the signal source generator must be disposed at a remote site in the patient's body."

As implied by the '311 patent, there are significant problems associated with existing systems and methods (such as in the '537 and '311 patents) for implanting a signal generator, infusion pump, or other device at a remote site in the patient's body, which result in tunneling of a catheter(s) or cable(s) through the neck and other areas of the body. For instance, tunneling a long cable through the neck can easily lead to lead damage and breakage. In addition, the long cable routed through the neck to the brain provides an extended track for infection directly into the brain. Also, surgical tunneling for the cable and placement of the signal generator require general anesthesia due to the large, broad area involved. General anesthesia has a rather high risk of mortality and morbidity vis-à-vis local anesthetic. In addition, the tunneling tool used for the long cable passes dangerously close to the common carotid artery and the jugular vein in the neck, with attendant risks of bleeding and stroke.

In addition to the above and other problems not acknowledged or addressed by the prior art, is the existence of areas in the brain of patients with mood and/or anxiety disorders with decreased activity compared with control subjects. For instance, the '537 patent teaches treating anxiety by decreasing neuronal activity in certain areas of the brain that exhibit increased activity.

BRIEF SUMMARY OF THE INVENTION

The invention disclosed and claimed herein provides systems and methods for introducing one or more stimulating drugs and/or applying electrical stimulation to one or more areas of the brain via a "skull-mounted" device. The stimulation may be used to treat mood and/or anxiety disorders. The findings described earlier suggest that electrical stimulation of specific sites in the brain may lead to profound changes in mood. For instance, the functional imaging and clinical studies described above suggest likely targets for Deep Brain Stimulation (DBS) as a therapy for depression.

Patients with mood and/or anxiety disorders will likely respond to therapeutic excitatory stimulation applied to those areas of the brain that exhibit chronic decreased activity relative to psychiatrically normal control subjects. Such excitatory stimulation is likely to be produced by low-frequency electrical stimulation, an excitatory neurotransmitter agonist, an inhibitory neurotransmitter antagonist, and/or a medication that increases levels of an excitatory neurotransmitter, such as Prozac® antidepressant (i.e., fluoxetine hydrochloride).

Patients with mood and/or anxiety disorders will likely respond to therapeutic inhibitory stimulation applied to those areas of the brain that exhibit chronic increased activity relative to psychiatrically normal control subjects. Such inhibitory stimulation is likely to be produced by high-frequency electrical stimulation, an inhibitory neurotransmitter agonist, an excitatory neurotransmitter antagonist, and/or a medication that increases the level of an inhibitory neurotransmitter.

The treatment provided by the invention is carried out by at least a system control unit (SCU). In one preferred form, and SCU comprises an implantable pulse generator (IPG) and implantable electrode(s) in the case of electrical stimulation only and an implantable pump and catheter(s) in the case of drug infusion only. However, an SCU preferably provides both electrical stimulation and one or more stimulating drugs when necessary and desired. In this embodiment, the SCU is preferably implanted in a surgically-created shallow depression in the temporal bone, with one or more electrode leads and/or catheters attached to the SCU running subcutaneously to an opening in the skull where they pass into or onto the brain parenchyma and surrounding tissue. In another preferred form of an SCU, a miniature implantable neurostimulator, such as a Bionic Neuron (also referred to as a BION™ microstimulator), is implanted. Preferred systems also include one or more sensors for sensing symptoms or other conditions that may indicate a need for treatment.

The SCU preferably includes a programmable memory for storing data and/or control stimulation parameters. This allows stimulation and control parameters to be adjusted to levels that are safe and efficacious with minimal discomfort. Electrical and drug stimulation may be controlled independently; alternatively, electrical and drug stimulation may be coupled, e.g., electrical stimulation may be programmed to occur only during drug infusion.

A preferred form of the invention uses one or more stimulating drugs and/or electrical stimulation to treat depression. According to one embodiment of the invention, the stimulation increases excitement of one or more of those areas of the brain that exhibit chronic decreased activity in patients relative to psychiatrically normal control subjects, thereby treating or preventing depression. Such excitatory stimulation is likely to be produced by low-frequency electrical stimulation, an excitatory neurotransmitter agonist(s) (e.g., norepinephrine), an inhibitory neurotransmitter antagonist(s), and/or a medication that increases the level of an excitatory neurotransmitter (e.g., Prozac® antidepressant). Additional uses of the present invention include the application to panic disorder, obsessive-compulsive disorder, and other mood and/or anxiety disorders.

According to another embodiment of the invention, the stimulation decreases excitement of one or more of those areas of the brain that exhibit chronic increased activity in patients relative to psychiatrically normal control subjects, thereby treating or preventing depression. Such inhibitory stimulation is likely to be produced by high-frequency electrical stimulation, an inhibitory neurotransmitter agonist(s) (e.g., Gamma-Aminobutyric Acid, or GABA), an excitatory neurotransmitter antagonist(s), and/or a medication that increases the level of an inhibitory neurotransmitter. Again, additional uses include the application to panic disorder, obsessive-compulsive disorder, and other mood and/or anxiety disorders.

According to a preferred embodiment of the invention, the electrodes used for electrical stimulation are arranged as an array on a very thin implantable lead. The SCU is programmed to produce either monopolar electrical stimulation, e.g., using the SCU case as an indifferent electrode, or to produce bipolar electrical stimulation, e.g., using one of the electrodes of an electrode array as an indifferent electrode. The SCU includes a means of stimulating a nerve or infusing a stimulating drug(s) either intermittently or continuously. Specific stimulation parameters may provide therapeutic advantages for, e.g., various forms of mood and/or anxiety disorders.

The SCU used with the present invention preferably possesses one or more of the following properties:

- at least two electrodes for applying stimulating current to surrounding tissue and/or a pump and at least one catheter for delivering a drug or drugs to surrounding tissue;
- electronic and/or mechanical components encapsulated in a hermetic package made from biocompatible material(s);
- an electrical coil inside the package that receives power and/or data by inductive or radio-frequency (RF) coupling to a transmitting coil placed outside the body, avoiding the need for electrical leads to connect devices to a central implanted or external controller;
- means for receiving and/or transmitting signals via telemetry;
- means for receiving and/or storing electrical power within the SCU; and
- a form factor making the SCU implantable in a depression or opening in the skull.

The power source of the SCU is preferably realized using one or more of the following options:

(1) an external power source coupled to the SCU via a radio-frequency (RF) link;
(2) a self-contained power source made using any means of generation or storage of energy, e.g., a primary battery, a replenishable or rechargeable battery, a capacitor, a supercapacitor; and/or
(3) if the self-contained power source is replenishable or rechargeable, a means of replenishing or recharging the power source, e.g., an RF link, an optical link, or other energy-coupling link.

According to one embodiment of the invention, an SCU operates independently. According to another embodiment of the invention, an SCU operates in a coordinated manner with other implanted SCUs, other implanted devices, or with devices external to the patient's body.

According to yet another embodiment of the invention, an SCU incorporates means of sensing the disorder or symptoms thereof, or other measures of the state of the patient.

Sensed information is preferably used to control the electrical and/or drug stimulation parameters of the SCU in a closed loop manner. According to one embodiment of the invention, the sensing and stimulating means are incorporated into a single SCU. According to another embodiment of the invention, the sensing means communicates sensed information to at least one SCU with stimulating means.

Thus, the present invention provides systems and methods for the treatment of mood and/or anxiety disorders that utilizes at least one compact, relatively inexpensive SCU. The implant site is preferably chosen to result in a relatively simple procedure, with the associated advantages in terms of reduced surgical time, expense, possible error, and opportunity for infection. Other advantages of the present invention include, inter alia, the system's monitoring and programming capabilities, the power source, storage, and transfer mechanisms, the activation of the device by the patient or clinician, the system's open loop capabilities and closed loop capabilities coupled with sensing a need for and/or response to treatment, and coordinated use of one or more SCUs.

BRIEF DESCRIPTION OF THE DRAWINGS

The above and other aspects, features, and advantages of the present invention will be more apparent from the following more particular description thereof, presented in conjunction with the following drawings wherein:

FIGS. 4B–4D depict coronal section views of the brain of FIG. 4A;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
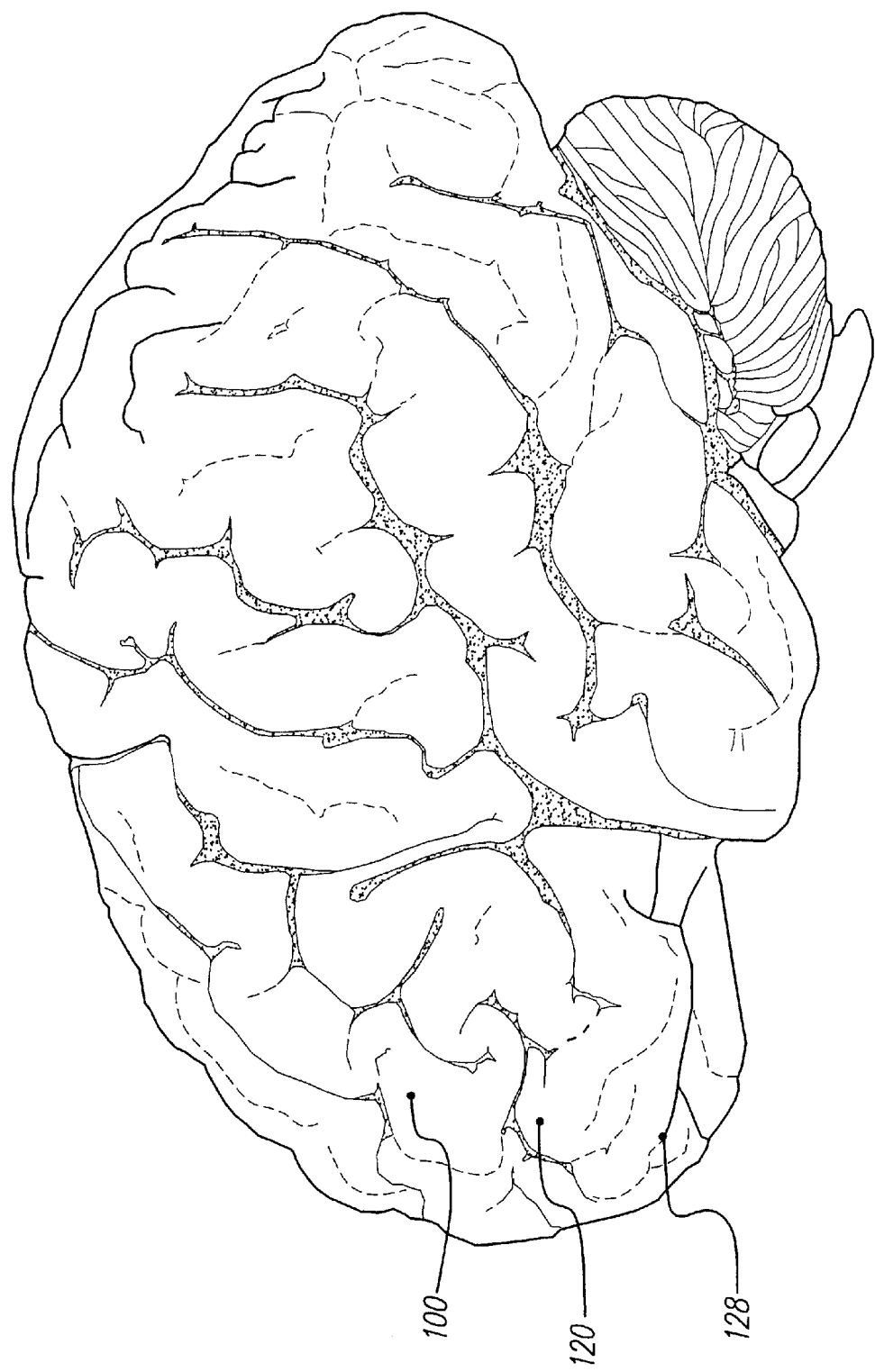
FIG. 1 depicts the lateral surface of the brain.
Figure 2:
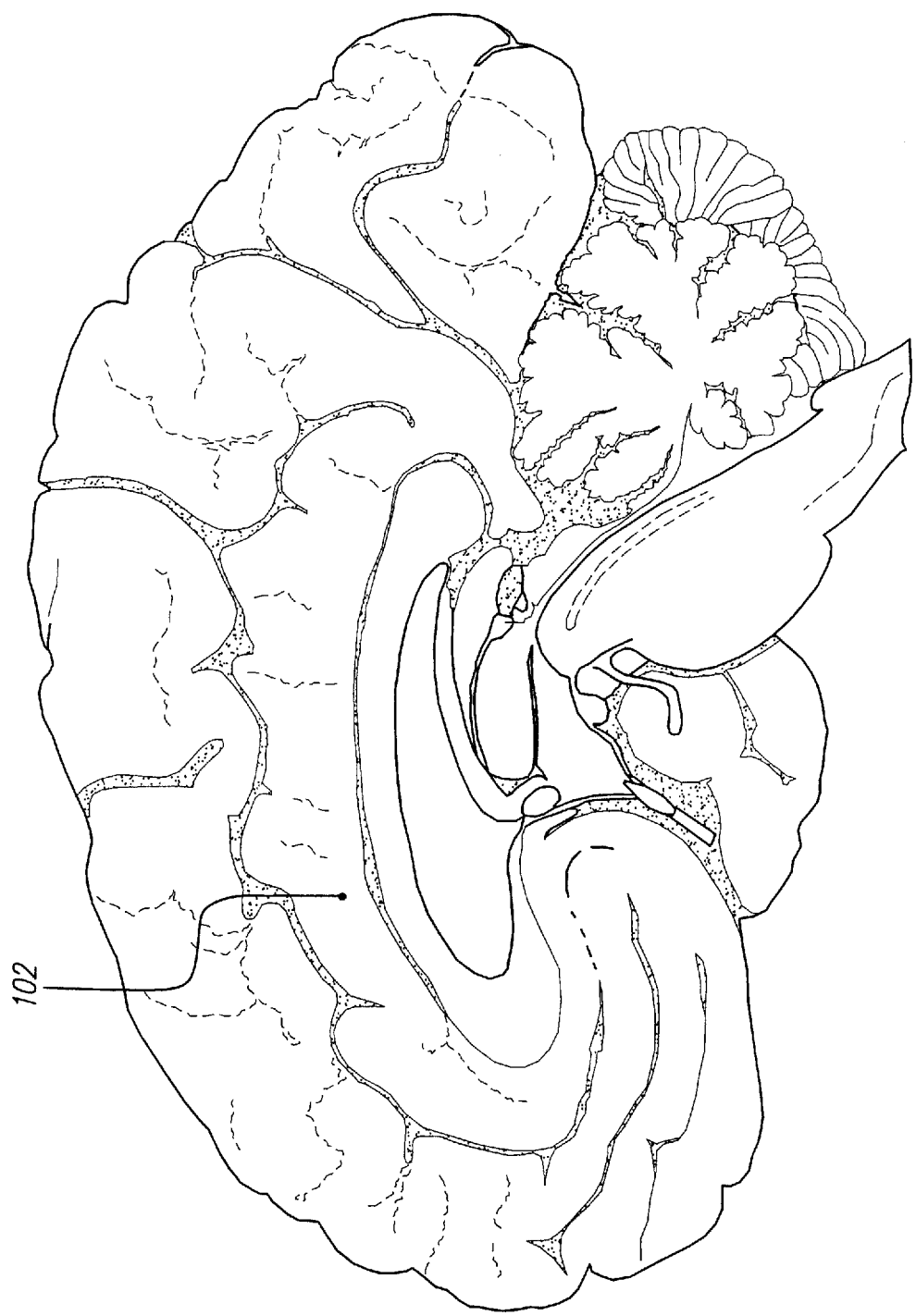
FIG. 2 depicts the medial surface of the brain.

As described above, decreased blood flow has been noted in the left dorsolateral prefrontal cortex (or medial frontal gyrus) of depressed patients, and was correlated with the severity of negative symptoms. FIG. 1 depicts the lateral surface of the brain, and shows the location of the dorsolateral prefrontal cortex 100. Similarly, the anterior cingulate gyrus has demonstrated decreased blood flow or metabolic activity in patients with depression, while increased activity has been noted in the anterior cingulate gyrus of patients responding to antidepressant medication. FIG. 2 depicts the medial surface of the brain, and indicates the location of the anterior cingulate gyrus 102.

Figure 3A:
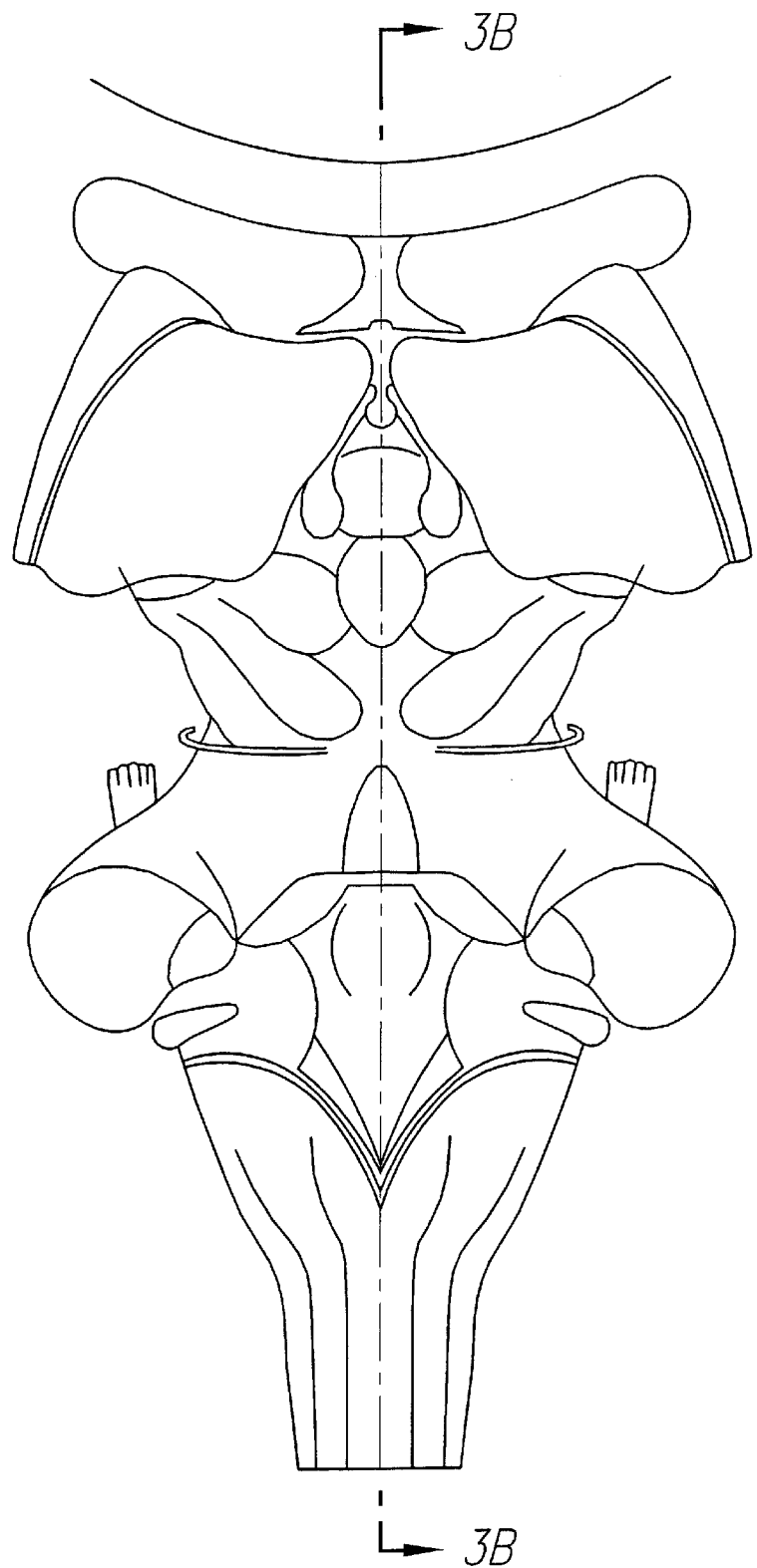
FIG. 3A depicts the dorsal surface of the brain stem.
Figure 3B:
FIG. 3B is a section view through the brain stem depicted in FIG. 3A.
Figure 4A:
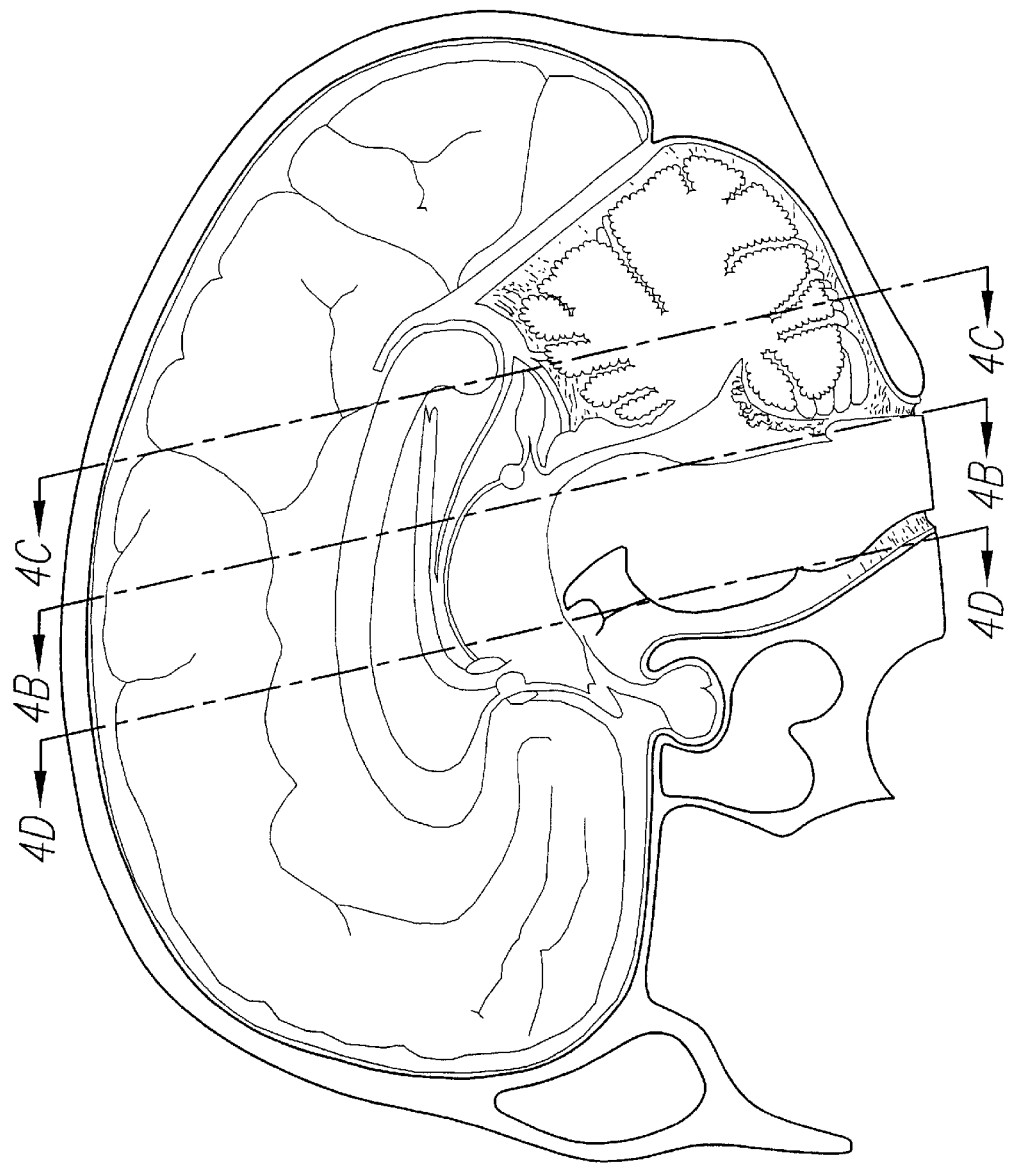
FIG. 4A depicts the medial surface of the head.
Figure 4B:
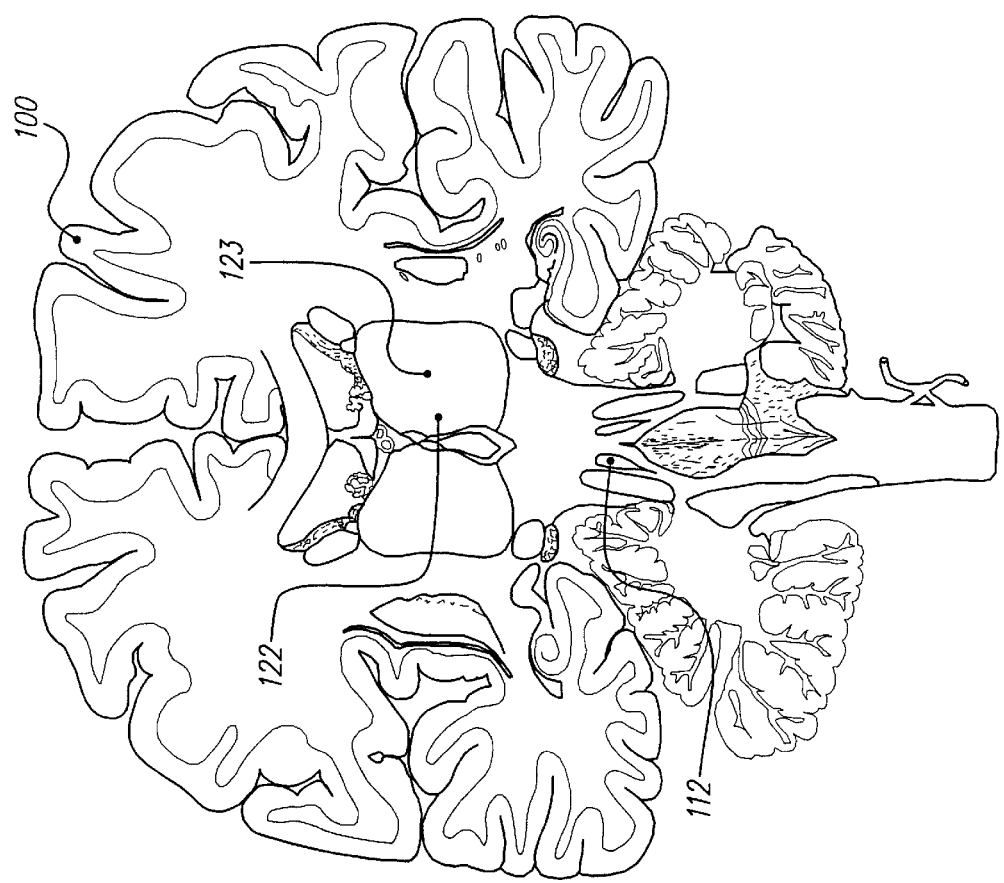

As noted above, levels of neurotransmitters and their receptors in the brains of patients with depression also indicate sites in the brain that are abnormal in depression. For example, an increase in serotonin receptors in the dorsal raphe nucleus has been implicated in suicide victims with major depression. An unusually large population of receptors may indicate that serotonin levels are unusually low. Furthermore, other indications suggest that decreased activity in the dorsal raphe nucleus may be related to depression. The location of the dorsal raphe nucleus 110 is shown in FIG. 3B. In addition, reduced levels of the neurotransmitter norepinephrine are found in the locus coeruleus of some patients with major depression. The location of the locus coeruleus 112 is shown in FIG. 4B.

As stated earlier, the median and dorsal raphe nuclei 110 have major serotonergic projections to the limbic system, and the locus coeruleus 112 has major noradrenergic projections to virtually the entire central nervous system, including the cerebral cortex, the hypothalamus, and the limbic system. In general, portions of the limbic system, which system is credited with roles in memory, emotion, and olfaction, often demonstrate decreased activity in depressed patients. For instance, areas that release serotonin, and areas responsible for norepinephrine produce less of these neurotransmitters in many depressed patients (for which the body may attempt to compensate with higher levels of receptors). Thus, via mechanisms described in more detail below, the present invention provides electrical stimulation, and/or excitatory neurotransmitter agonist(s), and/or inhibitory neurotransmitter antagonist(s), and/or medication that increases the level of an excitatory neurotransmitter to these areas or increases the level of neural activity in these areas.

Figure 4D:

In other cases of depression, increased activity is found in various locations within the brain. For instance, the ventral prefrontal cortex 120 (FIG. 1) demonstrates increased activity in some patients with depression. In addition, blood flow and metabolism are abnormally increased in the medial thalamus 122 (FIG. 4B) of some patients with Major Depression and Bipolar Disorder as compared with controls. Increased blood flow has also been seen in the cerebellar vermis 124 (FIG. 4C) of patients with depression-related cognitive impairment, while the metabolic rate in the right amygdala 126 (FIG. 4D) seems to predict negative affects in some depressed patients. Also, patients with obsessive-compulsive disorder have exhibited increased activity in the orbitofrontal cortex 128 (FIG. 1), anterior cingulate gyrus 102 (FIG. 2), thalamus 123 (FIG. 4B), and caudate nucleus 129 (FIG. 4D).

The present invention provides electrical and/or drug stimulation to one or more of the above mentioned areas as a treatment for mood and/or anxiety disorders. Herein, stimulating drugs comprise medications, anesthetic agents, synthetic or natural hormones, neurotransmitters, cytokines and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

In one preferred alternative, an implantable signal generator and electrode(s) and/or an implantable pump and catheter(s) are used to deliver electrical stimulation and/or one or more stimulating drugs to specific areas in the brain. One or more electrodes are surgically implanted in the brain to provide electrical stimulation, and/or one or more catheters are surgically implanted in the brain to infuse the stimulating drug(s).

Figure 5:
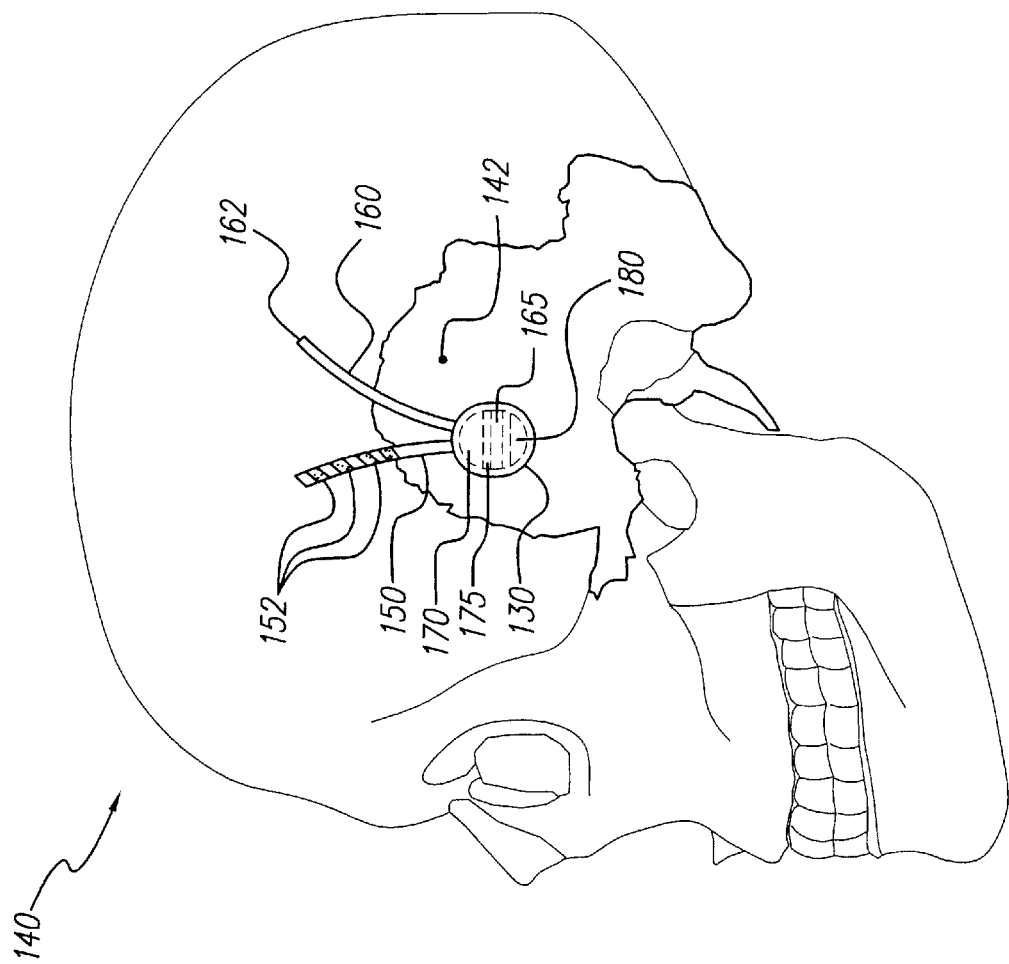
FIG. 5 illustrates a lateral view of the skull.

As depicted in FIG. 5, system control unit (SCU) 130 is preferably (but not necessarily) implanted beneath the scalp, more preferably in a surgically-created shallow depression or opening in the skull 140, and most preferably in temporal bone 142. SCU 130 preferably conforms to the profile of surrounding tissue(s) and/or bone(s), and is small and compact. This is preferable so that no unnecessary pressure is applied to the skin or scalp, as this may result in skin erosion or infection. SCU 130 preferably has a diameter of no greater than 75 mm, more preferably no greater than 65 mm, and most preferably about 35–55 mm. SCU thickness (e.g., depth into the skull) of approximately 10–12 mm is preferred, while a thickness of about 8–10 mm or less is more preferred.

One or more electrode leads 150 and/or catheters 160 attached to SCU 130 run subcutaneously, preferably in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) has the advantages of decreased likelihood of erosion of the overlying skin, and of minimal cosmetic impact.

In the case of treatment with electrical stimulation, electrode(s) 152 are carried on lead 150 having a proximal end coupled to SCU 130. The lead contains wires electrically connecting electrodes 152 to SCU 130. SCU 130 contains electrical components 170 that produce electrical stimulation pulses that travel through the wires of lead 150 and are delivered to electrodes 152, and thus to the tissue surrounding electrodes 152. To protect the electrical components inside SCU 130, the case of the SCU is preferably hermetically sealed. For additional protection against, e.g. impact, the case is preferably made of metal (e.g. titanium) or ceramic, which materials are also, advantageously, biocompatible. In addition, SCU 130 is preferably Magnetic Resonance Imaging (MRI) compatible.

In one alternative, the electrical stimulation may be provided as described in International Patent Application Serial Number PCT/US01/04417 (the '417 application), filed Feb. 12, 2001 (which claims priority to U.S. Provisional Patent Application Serial No. 60/182,486, filed Feb. 15, 2000), which application is incorporated herein by reference in its entirety. As such, the electrical stimulation of the present invention may be as provided in this PCT application, which is directed to a "Deep Brain Stimulation System for the Treatment of Parkinson's Disease or Other Disorders".

In yet another alternative, the electrical stimulation is provided by one or more implantable microstimulators, preferably of the type referred to as BION™ devices. The following documents describe various features and details associated with the manufacture, operation and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar 16, 1993 | Implantable Microstimulator |
| U.S. Pat. No. 5,193,540 | Issued Mar 16, 1993 | Structure and Method of Manufacture of an Implantable Microstimulator |
| U.S. Pat. No. 5,312,439 | issued May 17, 1994 | Implantable Device Having an Electrolytic Storage Electrode |
| U.S. Pat. No. 5,324,316 | Issued June 28, 1994 | Implantable Microstimulator |
| U.S. Pat. No. 5,405,367 | Issued April 11, 1995 | Structure and Method of Manufacture of an Implantable Microstimulator |
| PCT Publication WO 98/37926 | Published September 3, 1998 | Battery-Powered Patient Implantable Device |
| PCT Publication WO 98/43700 | Published October 8, 1998 | System of Implantable Devices For Monitoring and/or Affecting Body Parameters |
| PCT Publication WO 98/43701 | Published October 8, 1998 | System of Implantable Devices For Monitoring and/or Affecting Body Parameters |
| U.S. Pat. No. 6,051,017 (App. No. 09/077,662) | Issued April 18, 2000 | Improved Implantable Microstimulator and Systems Employing Same |
|  | Published September, 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

The microstimulator, when used, is preferably implanted with a surgical insertion tool specially designed for the purpose, or is injected (e.g., via a hypodermic needle). Alternatively, the device may be implanted via conventional surgical methods, or may be inserted using other endoscopic or laparoscopic techniques. A more complicated surgical procedure may be required for fixing the microstimulator in place.

In one preferred embodiment, the microstimulator comprises two, leadless electrodes. However, either or both electrodes may alternatively be located at the ends of short, flexible leads as described in U.S. Provisional Patent Application No. 60/156,980, filed Oct. 1, 1999 (now U.S. patent application Ser. No. 09/624,130, filed Jul. 24, 2000), which is incorporated herein by reference in its entirety. The use of such leads may permit electrical stimulation to be directed more locally to targeted tissue(s) a short distance from the surgical fixation of the bulk of the implantable stimulator, while allowing most elements of the microstimulator to be located in a more surgically convenient site. This minimizes the distance traversed and the surgical planes crossed by the device and any lead(s). In a preferred embodiment, the leads are no longer than about 50 mm.

As mentioned earlier, stimulation is provided in accordance with the teachings of the present invention by electrical stimulation and/or one or more stimulating drugs. The invention includes one or more system control units (SCU). In the case of electrical stimulation only, preferred SCUs include a microstimulator(s) and/or an implantable pulse/signal generator (IPG). In the case of drug infusion only, a preferred SCU comprises an implantable pump. In cases requiring both electrical stimulation and drug infusion, one or more SCUs are used. Alternatively and preferably, when needed, an SCU provides both electrical stimulation and one or more stimulating drugs.

In the case of treatment alternatively or additionally constituting drug infusion, catheter(s) 160 are coupled at a proximal end to SCU 130, which contains at least one pump 165 for storing and dispensing one or more drug(s) through the catheter(s) 160. Preferably at a distal end, catheter 160 has a discharge portion 162 for infusing dosages of the one or more drugs into a predetermined site in the brain tissue.

SCU 130 (which herein refers to IPGs, implantable pumps, IPG/pump combinations, microstimulators, and/or other alternative devices described herein) preferably contains electronic circuitry 170 for receiving data and/or power from outside the body by inductive, radio frequency (RF), or other electromagnetic coupling. In a preferred embodiment, electronic circuitry 170 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 130 also advantageously includes a programmable memory 175 for storing a set(s) of data, stimulation, and control parameters. This feature allows electrical and/or drug stimulation to be adjusted to settings that are safe and efficacious with minimal discomfort for each individual. Specific parameters may provide therapeutic advantages for various levels and types of mood and/or anxiety disorders. For instance, some patients may respond favorably to intermittent stimulation, while others may require continuous treatment for relief. Electrical and drug stimulation parameters are preferably controlled independently. However, in some instances, they are advantageously coupled, e.g., electrical stimulation may be programmed to occur only during drug infusion.

In addition, parameters may be chosen to target specific neural populations and to exclude others, or to increase neural activity in specific neural populations and to decrease neural activity in others. For example, relatively low frequency neurostimulation (i.e., less than about 50–100 Hz) typically has an excitatory effect on surrounding neural tissue, leading to increased neural activity, whereas relatively high frequency neurostimulation (i.e., greater than about 50–100 Hz) typically has an inhibitory effect, leading to decreased neural activity. Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof, and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, and metoprolol) and agents that decrease levels of excitatory neurotransmitters may inhibit neural activity.

The preferred SCU 130 also includes a power source and/or power storage device 180. Possible power options for a stimulation device of the present invention, described in more detail below, include but are not limited to an external power source coupled to the stimulation device, e.g., via an RF link, a self-contained power source utilizing any means of generation or storage of energy (e.g., a primary battery, a rechargeable battery such as a lithium ion battery, an electrolytic capacitor, or a super- or ultra-capacitor), and if the self-contained power source is replenishable or rechargeable, means of replenishing or recharging the power source (e.g., an RF link).

Figure 6:
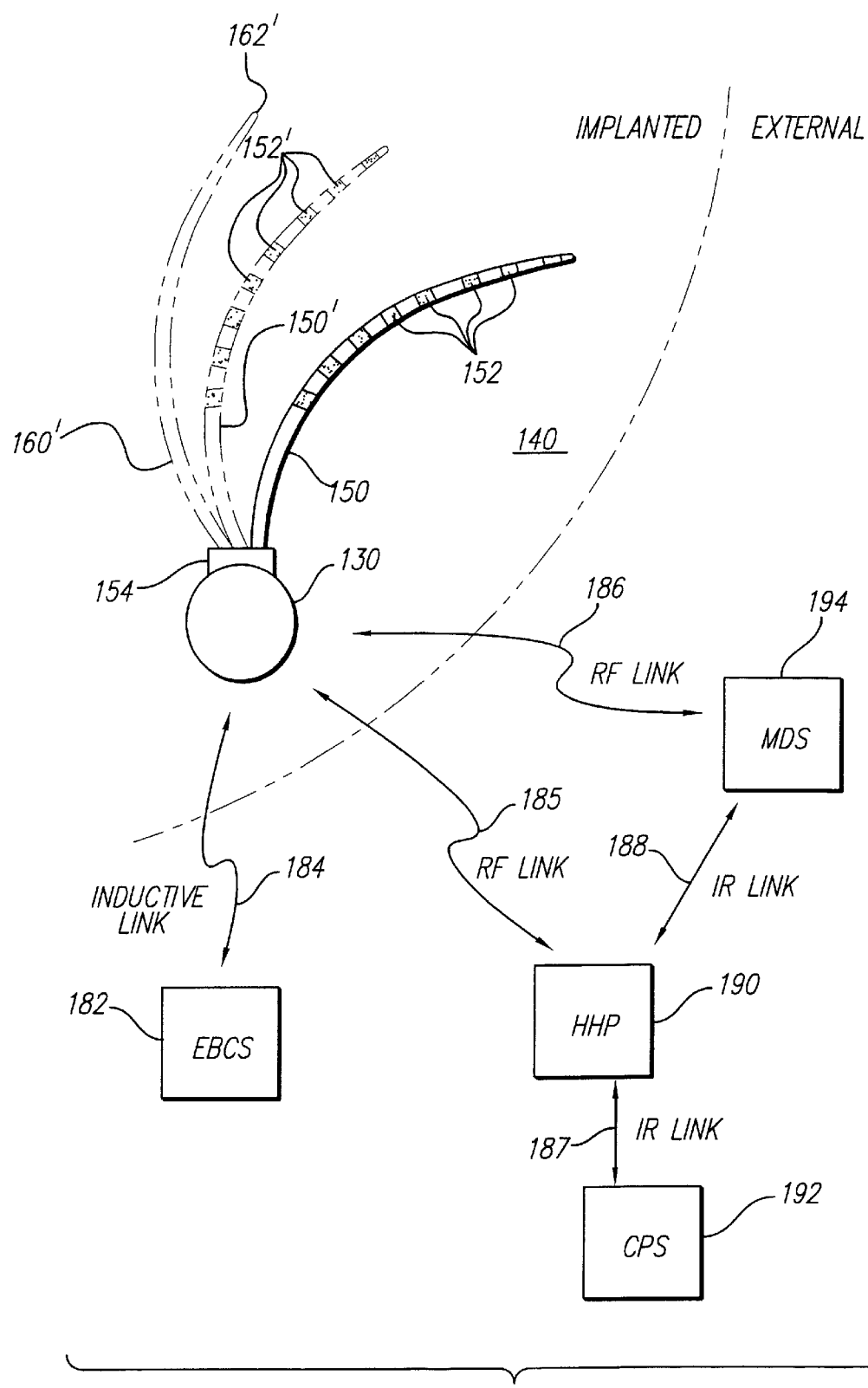
FIG. 6 illustrates internal and external components of an embodiment of the invention.

In one preferred embodiment shown in FIG. 6, SCU 130 includes a rechargeable battery as a power source/storage device 180. The battery is recharged, as required, from an external battery charging system (EBCS) 182, typically through an inductive link 184. In this embodiment, and as explained more fully in the earlier referenced '417 PCT application, SCU 130 includes a processor and other electronic circuitry 170 that allow it to generate stimulation pulses that are applied to the patient through electrodes 152 and/or catheter(s) 160 in accordance with a program and stimulation parameters stored in programmable memory 175. Stimulation pulses of drugs include various types and rates of infusion, such as intermittent infusion, infusion at a constant rate, and bolus infusion.

According to one preferred embodiment of the invention, such as described in the previously referenced '417 application and as depicted in FIG. 6, at least one lead 150 is attached to SCU 130, via a suitable connector 154. Each lead includes at least two electrodes 152, and may include as many as sixteen or more electrodes 152. Additional leads 150' and/or catheter(s) 160' may be attached to SCU 130. Hence, FIG. 6 shows (in phantom lines) a second catheter 160', and a second lead 150', having electrodes 152' thereon, also attached to SCU 130.

Lead(s) 150 are preferably less than 5 mm in diameter, and more preferably less than 1.5 mm in diameter. Electrodes 152, 152' are preferably arranged as an array, more preferably are at least two collinear electrodes, and more preferably at least 4 collinear electrodes. SCU 130 is preferably programmable to produce either monopolar electrical stimulation, e.g., using the SCU case as an indifferent electrode, or bipolar electrical stimulation, e.g., using one of the electrodes of the electrode array as an indifferent electrode. A preferred SCU 130 has at least four channels and drives up to sixteen electrodes or more.

According to one embodiment of the invention, an SCU operates independently. According to another embodiment of the invention, an SCU operates in a coordinated manner with other SCU(s), other implanted device(s), or other device(s) external to the patient's body. For instance, an SCU may control or operate under the control of another implanted SCU(s), other implanted device(s), or other device(s) external to the patient's body. An SCU may communicate with other SCUs, other implanted devices, and/or devices external to a patient's body via, e.g., an RF link, an ultrasonic link, or an optical link. Specifically, an SCU may communicate with an external remote control (e.g., patient and/or physician programmer) that is capable of sending commands and/or data to an SCU and that is preferably capable of receiving commands and/or data from an SCU.

For example, SCU 130 of the present invention may be activated and deactivated, programmed and tested through a hand held programmer (HHP) 190 (which may also be referred to as a patient programmer and is preferably, but not necessarily, hand held), a clinician programming system (CPS) 192 (which may also be hand held), or a manufacturing and diagnostic system (MDS) 194 (which may also be hand held). HHP 190 may be coupled to SCU 130 via an RF link 185. Similarly, MDS 194 may be coupled to SCU 130 via another RF link 186. In a like manner, CPS 192 may be coupled to HHP 190 via an infra-red link 187; and MDS 194 may be coupled to HHP 190 via another infra-red link 188. Other types of telecommunicative links, other than RF or infra-red may also be used for this purpose. Through these links, CPS 192, for example, may be coupled through HHP 190 to SCU 130 for programming or diagnostic purposes. MDS 194 may also be coupled to SCU 130, either directly through RF link 186, or indirectly through the IR link 188, HHP 190, and RF link 185.

Figure 7:
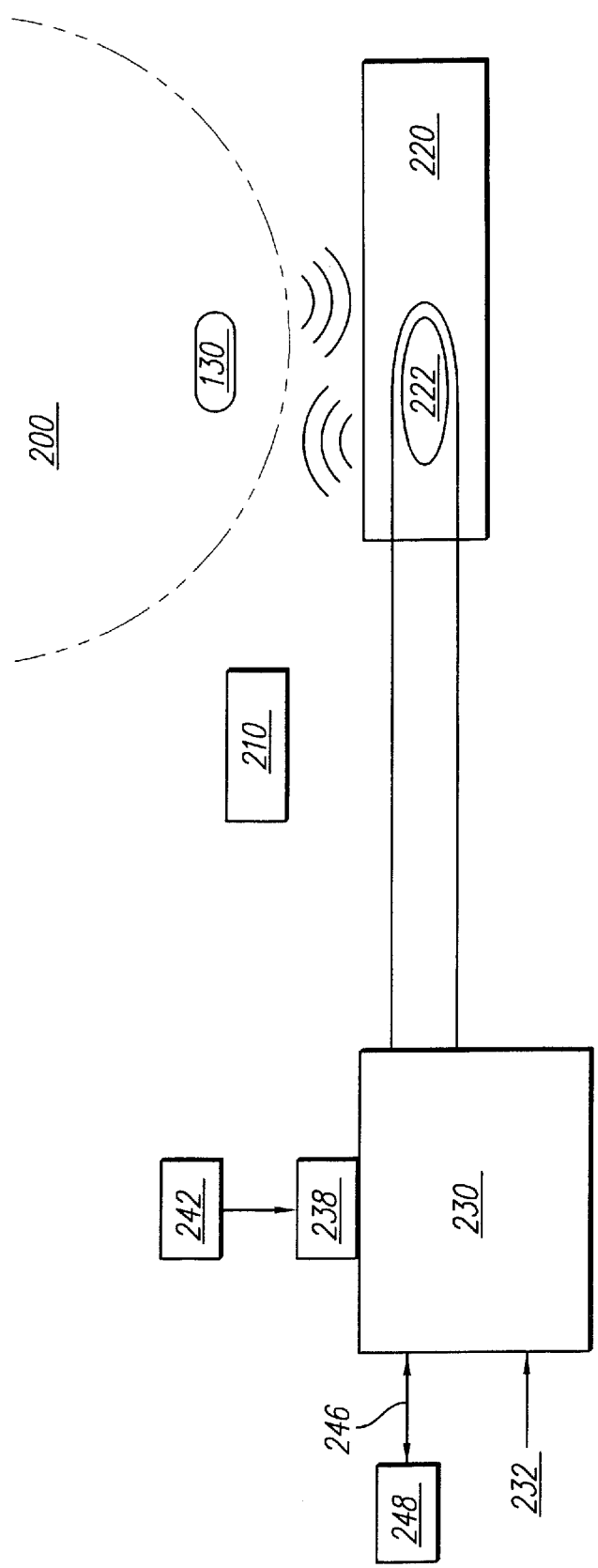
FIG. 7 illustrates external components of an embodiment of the invention.

In another preferred embodiment, using for example, a BION microstimulator(s) as described in the above referenced patents, and as illustrated in FIG. 7, the patient 200 switches SCU 130 on and off by use of controller 210, which is preferably handheld. Controller 210 operates to control SCU 130 by any of various means, including sensing the proximity of a permanent magnet located in controller 210, or sensing RF transmissions from controller 210.

External components for one preferred embodiment related to programming and providing power to SCU 130 are also illustrated in FIG. 7. When it is required to communicate with SCU 130, patient 200 is positioned on or near external appliance 220, which appliance contains one or more inductive coils 222 or other means of communication (e.g., RF transmitter and receiver). External appliance 220 is connected to or is a part of external electronic circuitry appliance 230 which receives power 232 from a conventional power source. External appliance 230 contains manual input means 238, e.g., a keypad, whereby the patient 200 or a caregiver 242 may request changes in the parameters of the electrical and/or drug stimulation produced during the normal operation of SCU 130. In this preferred embodiment, manual input means 238 includes various electromechanical switches and visual display devices that provide the patient and/or caregiver with information about the status and prior programming of SCU 130.

Alternatively or additionally, external electronic appliance 230 is preferably provided with an electronic interface means 246 for interacting with other computing means 248, such as by a serial interface cable or infrared link to a personal computer or to a telephone modem. Such interface means 246 thus permits a clinician to monitor the status of the implant and prescribe new stimulation parameters from a remote location.

The external appliance(s) may advantageously be embedded in a cushion, pillow, or hat. Other possibilities exist, including a head band or other structure that may be affixed to the patient's body or clothing.

In order to help determine the strength and/or duration of electrical stimulation and/or the amount and/or type(s) of stimulating drug(s) required to produce the desired effect, in one preferred embodiment, a patient's response to and/or need for treatment is sensed. For example, when electrodes and/or catheters of SCU 130 are implanted in or near the dorsal raphe nucleus 110, signals from a serotonin level sensor built into SCU 130 may be recorded. (As used herein, "near" means as close as reasonably possible to targeted tissue, including touching or even being positioned within the tissue, but in general, may be as far as about 150 mm from the target tissue.)

Alternatively, an "SCU" dedicated to sensory processes communicates with an SCU that provides the stimulation pulses. The implant circuitry 170 may, if necessary, amplify and transmit these sensed signals, which may be digital or analog. Other methods of determining the required electrical and/or drug stimulation include measuring the electrical activity of a neural population (e.g., EEG), measuring neurotransmitter levels and/or their associated breakdown product levels, measuring medication and/or other drug levels, hormone levels, and/or levels of any other bloodborne substance(s), changes in one or more of these, other methods mentioned herein, and others that will be evident to those of skill in the field upon review of the present disclosure. The sensed information is preferably used to control the stimulation parameters of the SCU(s) in a closed-loop manner.

For instance, in one embodiment of the present invention, a first and second "SCU" are provided. The second "SCU" periodically (e.g. once per minute) records serotonin levels (or the level of some other substance, or an amount of electrical activity, etc.), which it transmits to the first SCU. The first SCU uses the sensed information to adjust electrical and/or drug stimulation parameters according to an algorithm programmed, e.g., by a physician. For example, the amplitude of electrical stimulation may be increased in response to decreased serotonin levels. More preferably, one SCU performs both the sensing and stimulating functions.

While an SCU 130 may also incorporate means of sensing symptoms or other prognostic or diagnostic indicators of mood and/or anxiety disorders, e.g., via levels of a neurotransmitter or hormone, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 130. However, in some cases, it may not be necessary or desired to include a sensing function or device, in which case stimulation parameters are determined and refined, for instance, by patient feedback.

Thus, it is seen that in accordance with the present invention, one or more external appliances are preferably provided to interact with SCU 130 to accomplish one or more of the following functions:

Function 1: If necessary, transmit electrical power from the external electronic appliance 230 via appliance 220 to SCU 130 in order to power the device and/or recharge the power source/storage device 180. External electronic appliance 230 may include an automatic algorithm that adjusts electrical and/or drug stimulation parameters automatically whenever the SCU(s) 130 is/are recharged.

Function 2: Transmit data from the external appliance 230 via the external appliance 220 to SCU 130 in order to change the parameters of electrical and/or drug stimulation produced by SCU 130.

Function 3: Transmit sensed data indicating a need for treatment or in response to stimulation from SCU 130 (e.g., impedance, electrical activity of a neural population (e.g., EEG), neurotransmitter levels, levels of neurotransmitter breakdown products, medication levels, hormone levels, or other activity) to external appliance 230 via external appliance 220.

Function 4: Transmit data indicating state of the SCU 130 (e.g., battery level, drug level, electrical stimulation and/or infusion settings, etc.) to external appliance 230 via external appliance 220.

By way of example, a treatment modality for depression is carried out according to the following sequence of procedures:

1. An SCU 130 is implanted so that its electrodes 152 and/or catheter discharge portion 162 are located in or near the dorsal raphe nucleus 110. If necessary or desired, electrodes 152' and/or catheter discharge portion(s) 162' may additionally or alternatively be located in or near the anterior cingulate gyrus.

2. Using Function 2 described above (i.e., transmitting data) of external electronic appliance 230 and external appliance 220, SCU 130 is commanded to produce a series of excitatory electrical stimulation pulses, possibly with gradually increasing amplitude, and possibly while infusing gradually increasing amounts of an excitatory neurotransmitter, e.g., glutamate.

3. After each stimulation pulse, or at some other predefined interval, any change in neurotransmitter level or electrical activity of a neural population (e.g., EEG) resulting from the electrical and/or drug stimulation is sensed, preferably by one or more electrodes 152 and/or 152'. These responses are converted to data and telemetered out to external electronic appliance 230 via Function 3.

4. From the response data received at external appliance 230 from SCU 130, the stimulus threshold for obtaining a response is determined and is used by a clinician 242 acting directly 238 or by other computing means 248 to transmit the desired electrical and/or drug stimulation parameters to SCU 130 in accordance with Function 2.

5. When patient 200 desires to invoke electrical stimulation and/or drug infusion, patient 200 employs controller 210 to set SCU 130 in a state where it delivers a prescribed stimulation pattern from a predetermined range of allowable stimulation patterns.

6. To cease electrical and/or drug stimulation, patient 200 employs controller 210 to turn off SCU 130.

7. Periodically, the patient or caregiver recharges the power source/storage device 180 of SCU 130, if necessary, in accordance with Function 1 described above (i.e., transmit electrical power).

For the treatment of any of the various types and levels of mood and/or anxiety disorders, it may be desirable to modify or adjust the algorithmic functions performed by the implanted and/or external components, as well as the surgical approaches, in ways that would be obvious to skilled practitioners of these arts. For example, it may be desirable to employ more than one SCU 130, each of which could be separately controlled by means of a digital address. Multiple channels and/or multiple patterns of electrical and/or drug stimulation might thereby be programmed by the clinician and controlled by the patient in order to deal with complex or multiple symptoms or dysfunctions, such as a mood disorder comorbid with an anxiety disorder.

In one preferred embodiment, SCU 130, or a group of two or more SCUs, is controlled via closed-loop operation. A need for and/or response to stimulation is sensed via SCU 130, or by an additional SCU (which may or may not be dedicated to the sensing function), or by another implanted or external device.

If necessary, the sensed information is transmitted to SCU 130. Preferably, the parameters used by SCU 130 are automatically adjusted based on the sensed information. Thus, the electrical and/or drug stimulation parameters are adjusted in a closed-loop manner to provide stimulation tailored to the need for and/or response to the electrical and/or drug stimulation.

According to another preferred embodiment of the invention, the electrical and/or drug stimulation increases excitement of one or more of those areas of the brain that exhibit chronic decreased activity in patients with mood and/or anxiety disorders relative to psychiatrically normal control subjects. Such excitatory stimulation is likely to be produced by low-frequency electrical stimulation (e.g., less than about 50–100 Hz), an excitatory neurotransmitter agonist(s) (e.g., norepinephrine, epinephrine, glutamate, acetylcholine, serotonin, dopamine), an agonist thereof, an inhibitory neurotransmitter antagonist(s) (e.g., bicicilline), an agent that increases the level of an excitatory neurotransmitter (e.g., edrophonium, Mestinon), and/or an agent that decreases the level of an inhibitory neurotransmitter. Therefore, as described above, stimulation may be applied to one or more of the anterior cingulate gyrus, dorsal prefrontal cortex (especially the left dorsolateral prefrontal cortex), the dorsal and/or median raphe nuclei, and/or the locus coeruleus.

According to yet another preferred embodiment of the invention, the electrical and/or drug stimulation decreases excitement of one or more of those areas of the brain that exhibit chronic increased activity in patients with mood and/or anxiety disorders relative to psychiatrically normal control subjects. Such inhibitory stimulation is likely to be produced by high-frequency electrical stimulation (e.g., greater than about 50–100 Hz), an inhibitory neurotransmitter agonist(s) (e.g., dopamine, glycine, GABA), an agonist thereof, an excitatory neurotransmitter antagonist(s) (e.g., prazosin, metoprolol), an agent that increases the level of an inhibitory neurotransmitter, an agent that decreases the level of an excitatory neurotransmitter, and/or a local anesthetic agent (e.g., lidocaine) is likely to produce such inhibition. Thus, stimulation may also/instead be applied to one or more of the ventral prefrontal cortex, the cerebellar vermis, the amygdala, the orbitofrontal cortex, the caudate nucleus, the medial thalamus, and/or other areas of the thalamus.

In yet another alternative, sensing means described earlier may be used to orchestrate first the activation of SCU(s) targeting one or more areas of the brain, and then, when appropriate, the SCU(s) targeting another area and/or by a different means. Alternatively, this orchestration may be programmed, and not based on a sensed condition.

Thus, the present invention provides systems and methods for the treatment, control, and/or prevention of mood and/or anxiety disorders that utilize one or more compact, relatively inexpensive SCUs. The implant site results in a relatively simple procedure, with the associated advantages in terms of reduced surgical time, expense, possible error, and opportunity for infection and other complications. Other advantages, inter alia, of the present invention include the system's monitoring and programming capabilities, the power source, storage, and transfer mechanisms, the activation of the device by the patient or clinician, the system's open-loop capabilities and closed-loop capabilities coupled with sensing a need for and/or response to treatment, and coordinated use of one or more SCUs.

While the invention herein disclosed has been described by means of specific embodiments and applications thereof, numerous modifications and variations could be made thereto by those skilled in the art without departing from the scope of the invention set forth in the claims.

What is claimed is:

1. A method of treating patients with mood and/or anxiety disorders, comprising:

implanting at least one system control unit in the skull or the brain of the patient, wherein the at least one unit controls the delivery of at least one stimulus to at least one area of the brain affecting mood and/or anxiety disorders;

applying the at least one stimulus to the at least one area of the brain in order to at least in part alleviate symptoms of the mood and/or anxiety disorder of the patient being treated, wherein the at least one stimulus increases excitement of the at least one area of the brain affecting mood and/or anxiety disorders that exhibits chronic decreased activity; and wherein the at least one stimulus is applied to one or more of the anterior cingulate gyrus, the dorsal prefrontal cortex, the dorsal raphe nuclei, the median raphe nuclei, and the locus coeruleus.

2. The method of treatment of claim 1 wherein the system control unit is connected to at least two electrodes, and wherein the stimulus comprises electrical stimulation delivered via the at least two electrodes.

3. The method of treatment of claim 1 wherein the system control unit is connected to at least one catheter, and wherein the stimulus comprises stimulation via one or more drugs delivered through the at least one catheter.

4. The method of treatment of claim 1 wherein the system control unit is connected to at least two electrodes and to at least one catheter, and wherein the stimulus comprises both electrical stimulation delivered via the at least two electrodes and stimulation via one or more drugs delivered through the at least one catheter.

5. The method of claim 1 wherein the stimulation is electrical stimulation delivered at a frequency less than about 100 Hz.

6. The method of claim 1 wherein the stimulation is drug stimulation provided by at least one of an excitatory neurotransmitter agonist, an inhibitory neurotransmitter antagonist, an agent that increases the level of an excitatory neurotransmitter, and an agent that decreases the level of an inhibitory neurotransmitter.

7. The method of claim 6 wherein the excitatory drug is at least one of norepinephrine, epinephrine, glutamate, acetylcholine, serotonin, dopamine, and an agonist thereof.

8. The method of claim 1 further comprising sensing at least one condition and using the at least one sensed condition to automatically determine the stimulus to apply.

9. The method of claim 8 wherein the at least one sensed condition is one or more of serotonin level, electrical activity of a neural population, a neurotransmitter level, change in a neurotransmitter level, a neurotransmitter breakdown product level, change in a neurotransmitter breakdown product level, a medication level, change in a medication level, a drug level, change in a drug level, a hormone level, change in a hormone level, level of a bloodborne substance, change in level of a bloodborne substance.

10. A method of treating patients with mood and/or anxiety disorders, comprising:

implanting at least one system control unit in the skull or the brain of the patient, wherein the at least one unit controls the delivery of at least one stimulus to at least one area of the brain affecting mood and/or anxiety disorders;

applying the at least one stimulus to the at least one area of the brain in order to at least in part alleviate symptoms of the mood and/or anxiety disorder of the patient being treated, wherein the at least one stimulus decreases excitement of at least one area of the brain affecting mood and/or anxiety disorders that exhibits chronic increased activity; and wherein the at least one stimulus is applied to the cerebellar vermis.

11. The method of claim 10 wherein the stimulation is electrical stimulation delivered at a frequency greater than about 100 Hz.

12. The method of claim 10 wherein the stimulation is drug stimulation provided by at least one of an inhibitory neurotransmitter agonist, an excitatory neurotransmitter antagonist, an agent that increases the level of an inhibitory neurotransmitter, an agent that decreases the level of an excitatory neurotransmitter, and a local anesthetic agent.

13. The method of claim 12 wherein the inhibitory drug is at least one of GABA, glycine, dopamine, an agonist thereof, and lidocaine.

14. The method of claim 10 wherein the system control unit is connected to at least two electrodes, and wherein the stimulus comprises electrical stimulation delivered via the at least two electrodes.

15. The method of claim 10 wherein the system control unit is connected to at least one catheter, and wherein the stimulus comprises stimulation via one or more drugs delivered through the at least one catheter.

16. The method of claim 10 wherein the system control unit is connected to at least two electrodes and to at least one catheter, and wherein the stimulus comprises both electrical stimulation delivered via the at least two electrodes and stimulation via one or more drugs delivered through the at least one catheter.

17. The method of claim 10 further comprising sensing at least one condition and using the at least one sensed condition to automatically determine the stimulus to apply.

18. The method of claim 17 wherein the at least one sensed condition is one or more of serotonin level, electrical activity of a neural population, a neurotransmitter level, change in a neurotransmitter level, a neurotransmitter breakdown product level, change in a neurotransmitter breakdown product level, a medication level, change in a medication level, a drug level, change in a drug level, a hormone level, change in a hormone level, level of a bloodborne substance, change in level of a bloodborne substance.

* * * * *